United States Patent [19]

Pasulka

[11] Patent Number: 5,479,953
[45] Date of Patent: Jan. 2, 1996

[54] PORTABLE INTRAVENOUS EQUIPMENT CONSOLE AND WALKER APPARATUS FOR AN AMBULATORY PATIENT

[76] Inventor: Patrick S. Pasulka, 6808 N. 18th St., Paradise Valley, Ariz. 85253

[21] Appl. No.: 168,423

[22] Filed: Dec. 20, 1993

[51] Int. Cl.⁶ ........................................................ A45B 3/00
[52] U.S. Cl. .............................. 135/66; 135/67; 248/129; 604/905; 5/86.1
[58] Field of Search ................................. 135/66, 67, 72; 248/125, 129, 311.3; 5/86.1, 503.1, 662, 658, 81.1; 604/905; 128/912, DIG. 26

[56] References Cited

U.S. PATENT DOCUMENTS

| | | | |
|---|---|---|---|
| 3,483,574 | 12/1969 | Belnap | 5/86.1 |
| 4,262,872 | 4/1981 | Kodet | 248/311.3 |
| 4,332,378 | 6/1982 | Pryor | 135/67 X |
| 4,725,027 | 2/1988 | Bekanich | 248/129 X |
| 4,768,241 | 9/1988 | Beney | 5/503.1 X |
| 4,946,455 | 8/1990 | Rosen | 604/905 X |
| 4,985,947 | 1/1991 | Ethridge | 5/86.1 X |

OTHER PUBLICATIONS

"Molift Partner", Actuator, Oct. 8, 1993.

Primary Examiner—Lanna Mai
Attorney, Agent, or Firm—H. Gordon Shields

[57] ABSTRACT

A walker cart for an ambulatory patient includes a telescoping rod with a holder at the top end of the rod for holding one or more intravenous solution bags to which the patient is connected, and frame members to which infusion pump elements may be connected for the patient. The cart includes caster wheels for maneuvering the cart and handle elements which may be grasped by the ambulatory patient in several different ways, according to the desiderata or capability of the ambulatory patient.

22 Claims, 2 Drawing Sheets

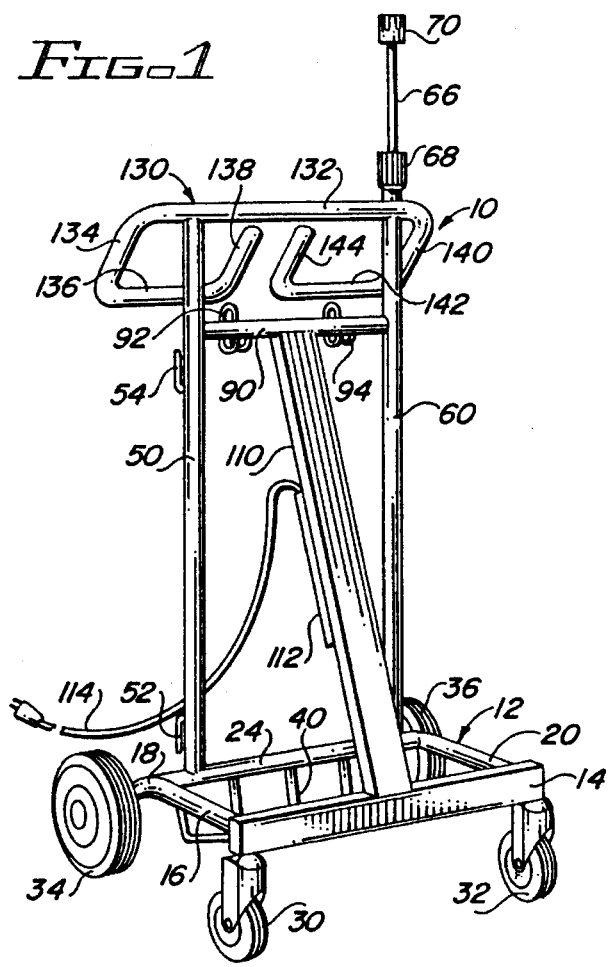
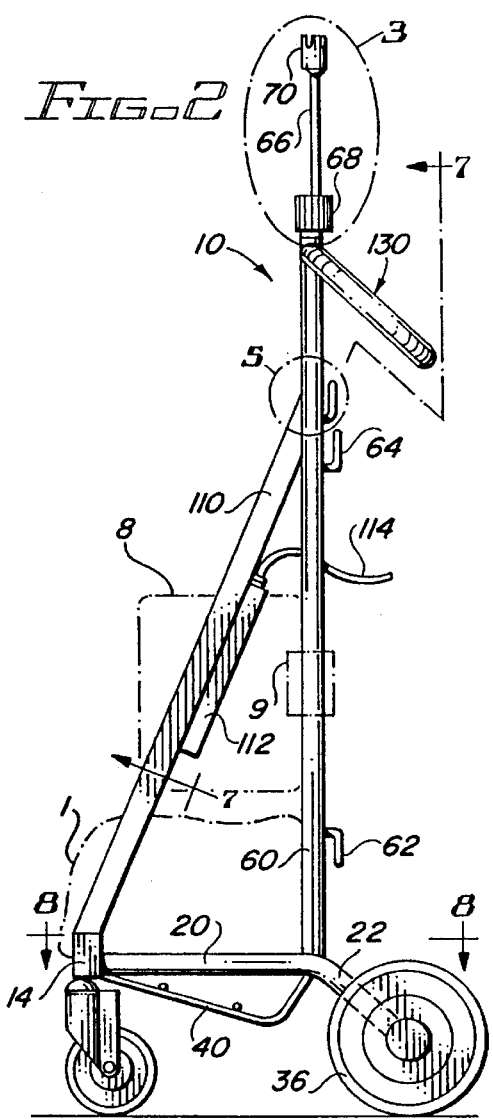
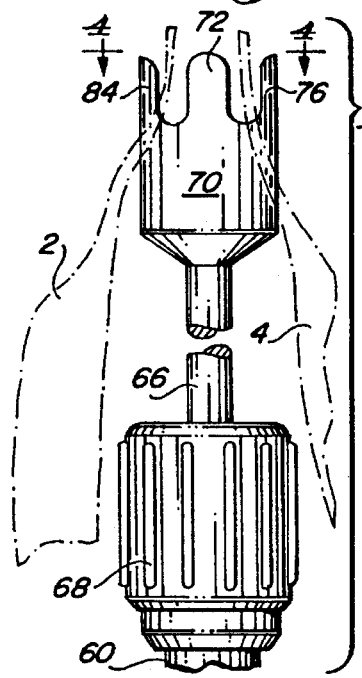
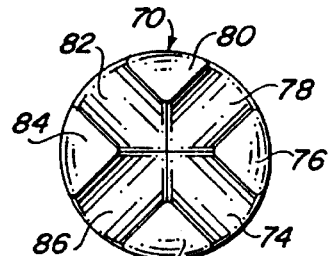
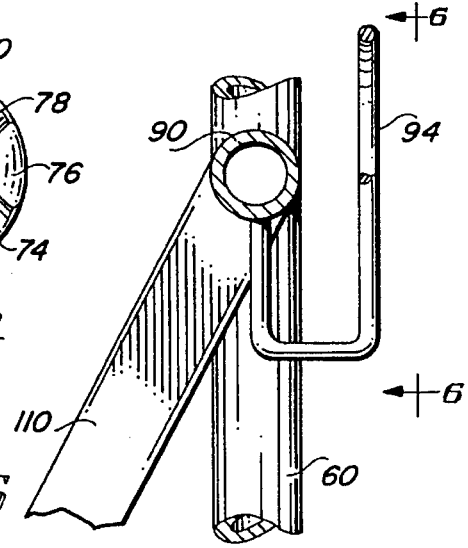

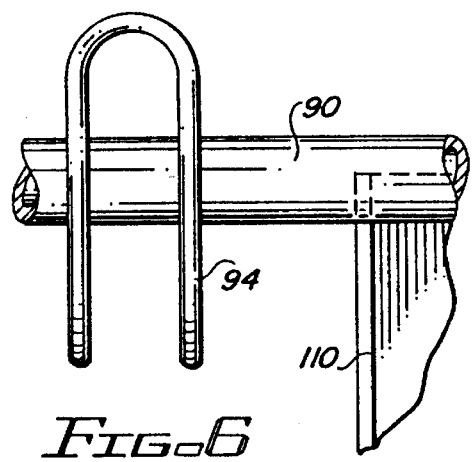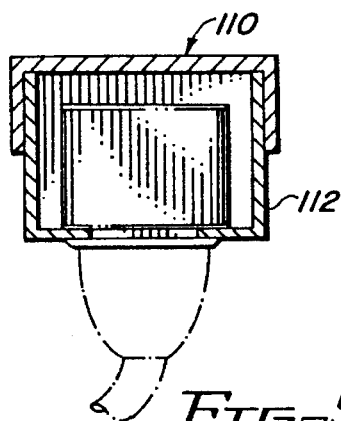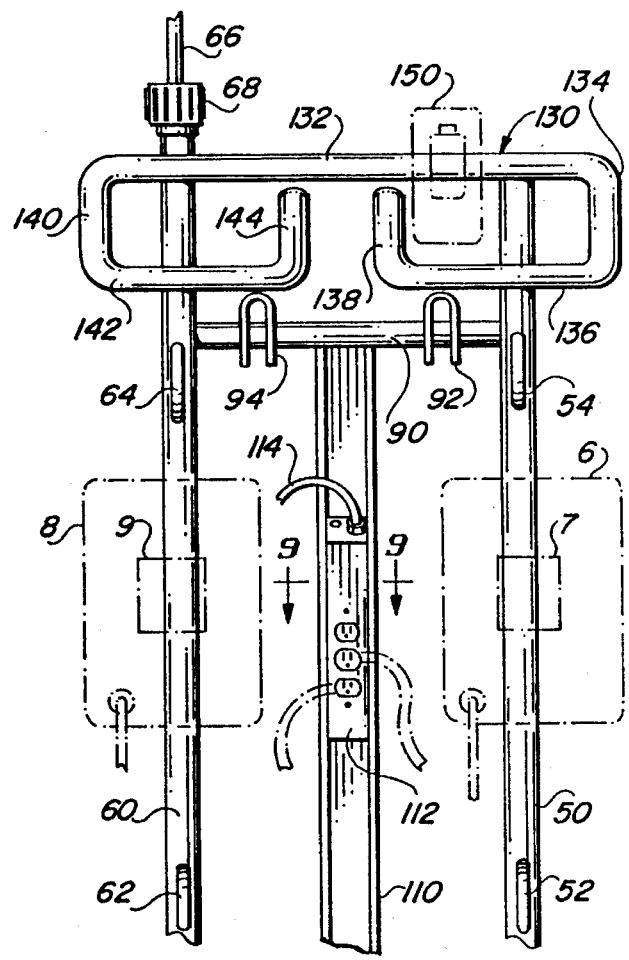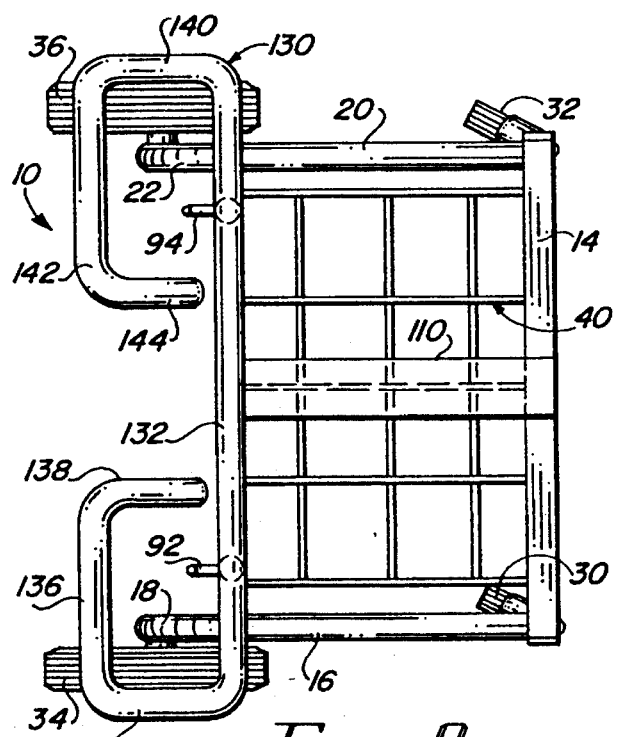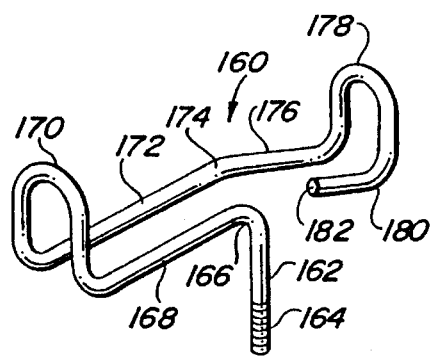

PORTABLE INTRAVENOUS EQUIPMENT CONSOLE AND WALKER APPARATUS FOR AN AMBULATORY PATIENT

BACKGROUND OF THE INVENTION

1. Field of the Invention

This invention relates to a stand for holding one or more intravenous solutions and pumps and which is movable with an ambulatory patient connected to the intravenous solution or solutions.

2. Description of the Prior Art

U.S. Pat. No. 3,704,025 (Cerveny et al) discloses a folding cart with wheels on the cart and a rear frame for supporting various elements. The rear frame also includes wheels. The cart includes a seat on which a user sits.

U.S. Pat. No. 4,251,044 (Olson) discloses an oxygen walker cart. The cart includes four wheels, an oxygen cylinder, a platform or table which comprises an arm rest for a user, and an extensible or telescoping rod for holding an I.V. container.

U.S. Pat. No. 4,332,378 (Pryor) discloses a wheeled stand with a circular hand grip portion to which a user may grasp for movement purposes. Extending upwardly from the center of the apparatus is a telescoping rod with provisions for holding an I.V. container.

U.S. Pat. No. 4,511,157 (Wilt) discloses a wheeled stand adapted to be connected to a wheel chair. The stand includes a pole to which an I.V. container may be secured.

U.S. Pat. No. 4,725,027 (Bekanich) discloses a wheeled stand which includes a telescoping rod for supporting I.V. equipment. The telescoping stand may be removed from the wheeled base and secured directly to a patient transport vehicle.

U.S. Pat. No. 4,765,355 (Kent) discloses a wheeled walking device for use with an ambulatory patient. The apparatus includes four wheels and a framework extending upwardly from the base to which a patient may hold or grasp for support and for moving the apparatus. Baskets or other elements may be secured to the apparatus for carrying items for use by the user of the apparatus.

U.S. Pat. No. 4,832,294 (Eidem) discloses a portable I.V. stand which includes a wheel base and a telescoping pole extending upwardly from the base. Various elements may be secured to the base and to the pole, including oxygen cylinders, an I.V. pump, an I.V. container, and the like. The base includes three wheels.

U.S. Pat. No. 4,892,279 (Lafferty et al) discloses a wheeled I.V. stand which includes four legs and a telescoping pole extending upwardly from the legs. The telescoping pole terminates upwardly in holding elements for supporting I.V. containers. The legs may be folded for storage purposes.

U.S. Pat. No. 4,905,944 (Jost et al) discloses an I.V. stand which includes a wheeled base and a telescoping rod for supporting I.V. containers. The telescoping rod also includes provisions for I.V. pumps. A single handle extends outwardly from the telescoping pole for moving and maneuvering the apparatus.

U.S. Pat. No. 5,000,407 (Juji et al) discloses a stand designed for holding a plurality of bags. The apparatus is designed for blood gathering purposes. Included are a base platform to which are secured four legs, a pole extending upwardly from the base platform, a horizontal platform arrangement, and a vertical panel also secured to the vertical post. At the top of the vertical post are holders for bags of blood.

U.S. Pat. No. 5,046,748 (Oat-Judge) discloses a walker with an automatic brake system. The apparatus includes a frame, with four wheels at the bottom of the frame. A bin supported on a platform between the legs, and handle elements which extend upwardly from the base. The handle elements include a horizontal element to which brake levers are secured. The user of the apparatus holds on to the brake levers to release the brakes. When the user releases the brake levers, the brakes are automatically set.

U.S. Pat. No. 5,048,849 (Mathews et al) discloses a change stroller which includes four wheels on a base, and a framework extending upwardly from the wheeled base. Various embodiments are illustrated, with various elements secured to the wheels.

Of the prior art patents discussed above, several of them are designed for ambulatory patients, and the movement of the apparatus typically includes merely a horizontal rod or structural member which may be grasped by a user of the apparatus. Under some circumstances, such a horizontal rod may be inconvenient for various ambulatory patients.

The holder for intravenous solution bags typically include a horizontally extending rod with hooks or the like on the rod for holding the I.V. containers. The I.V. containers are accordingly spread outwardly from the main support pole.

The above noted limitations of the prior art are overcome by the apparatus of the present invention in which handle elements are provided with several different provisions for grasping or holding by a user. I.V. containers are supported adjacent to each other and adjacent to the pole element which supports them.

SUMMARY OF THE INVENTION

The invention described and claimed herein comprises a walker cart movable with a patient, and to which a patient may hold for support in walking, and the cart may hold a plurality of intravenous solutions and infusion pumps for pumping the solutions into the patient. The cart includes caster wheels for providing maneuverability for the cart and a handle which may be conveniently grasped by a user in any of several different ways, as desired by a particular patient. The cart also includes vertical stanchions to which infusion pumps may be secured and a vertically telescoping rod for holding one or more intravenous solution bags.

Among the objects of the present invention are the following:

To provide new and useful intravenous solution bag holder;

To provide new and useful walker apparatus for an ambulatory patient and which cart includes a rod for holding an I.V. solution;

To provide new and useful intravenous solution holder apparatus including a stanchion for holding an infusion pump and a rod for holding an intravenous solution;

To provide new and useful cart apparatus for providing an ambulatory patient connected to an intravenous solution with a holder for the intravenous solution, a pump for pumping the solution, and electrical elements for operating the pump.

To provide new and useful cart apparatus for holding an I.V. solution, and an infusion pump, and a handle for use by a patient connected to the I.V. solution; and To provide new and useful cart apparatus having a holder head for holding a plurality of I.V. bags and a handle graspable by a patient connected to the I.V. bags.

BRIEF DESCRIPTION OF THE DRAWING

FIG. 1 is a perspective view of the apparatus of the present invention.

FIG. 2 is a side view of the apparatus of FIG. 1.

FIG. 3 is an enlarged view of a portion of the apparatus of the present invention taken generally from oval 3 of FIG. 2.

FIG. 4 is a view taken generally along line 4—4 of FIG. 3.

FIG. 5 is an enlarged view in partial section taken generally along circle 5 of FIG. 2.

FIG. 6 is an enlarged view taken generally along line 6—6 of FIG. 5.

FIG. 7 is a view taken generally along line 7—7 of FIG. 2.

FIG. 8 is a view in partial section taken generally along line 8—8 of FIG. 2.

FIG. 9 is a view in partial section taken generally along line 9—9 in FIG. 7.

FIG. 10 is a perspective view of an alternate embodiment of a portion of the present invention.

DESCRIPTION OF THE PREFERRED EMBODIMENT

FIG. 1 is a perspective view of portable intravenous equipment console and walker apparatus 10 of the present invention.

FIG. 2 comprises a side view of the apparatus 10 of the present invention. For the following discussion of the apparatus 10, reference will primarily be made to FIGS. 1 and 2. Other Figs. will be referred to as appropriate.

The apparatus 10 includes a base 12 which is wheeled for movement. The base 12 includes a front frame member 14, a pair of side frame members, including a side frame member 16 and a side frame member 20. A rear frame member 24 is secured to the side frame members 16 and 20. The rear frame member 24 is generally parallel to the front frame member 14. A pair of front caster wheels 30 and 32 are secured to and extend downwardly from the outer end of the front frame member 14.

A rear side frame member 18 extends downwardly at an angle from about the juncture of the side member 14 and the rear frame member 24. A relatively large wheel 34 is appropriately secured to the rear side frame member 18.

A rear side frame member 22 extends rearwardly and downwardly from about the juncture of the side frame member 22 and the rear frame member 24. A wheel 36 is appropriately secured to the rear side frame member 22. The rear wheels 34 and 36 are generally parallel to each other.

Disposed within the base 24, and specifically within the frame members 14, 16, 20, and 24, is a lower basket assembly or shelf 40. The basket assembly or shelf 40 generally comprises a wire frame or grid. The basket 40 is shown in FIGS. 1 and 2 and is shown in more detail in FIG. 8. FIG. 8 comprises a top view of the apparatus 10.

As may be seen from FIG. 8, as well as from FIGS. 1 and 2, the lower basket shelf 40 comprises a wire frame or grid having a plurality of longitudinal wire elements appropriately secured to the front frame member 14 and to the rear frame member 24 and to each other. The grid or frame also includes a plurality of transversely extending wire elements which are appropriately secured to the longitudinal frame elements.

As may be seen from FIGS. 1 and 2, the longitudinal frame members are bent in that they extend rearwardly and downwardly from the front frame member 14 and then upwardly to the rear frame member 24. The configuration of the basket 40 helps to retain goods disposed or supported therein. In FIG. 2, a bag or bundle of goods 1 is shown in dash dot line disposed in the basket 40. The bag or bundle 1 may be any appropriate goods, or bundle of goods, as desired.

Since the basket 40 is rather low, the weight of the goods 1 is disposed low on the apparatus 10, and the center of gravity of the goods 1 is also quite low, which may contribute to the stability of the apparatus 10, instead of contributing to its instability.

Extending upwardly from the base 12 are two vertical frame members. The vertical frame members include a vertical frame member 50 and a vertical frame member 60. The vertical frame members 50 and 60 extend upwardly from the rear frame member 24. The vertical frame members 50 and 60 are generally parallel to each other. They are appropriately secured to the bottom frame member 24 and extend upward generally perpendicularly thereto.

For convenience in securing various elements, such as electrical cords, to the vertical frame members 50 and 60, there are hook elements secured to the frame members 50 and 60 at the rear thereof, or remote from the front of the apparatus 10. The front of the apparatus 10 is defined by the front frame member 14 and the basket 40. The hook elements include a lower hook element 52 and an upper hook element 54 secured to the frame member 50, and a lower hook element 62 and an upper hook element 64 secured to the vertical frame member 60.

A rod 66 extends upwardly from the vertical frame member 60. The rod 66 telescopes relative to the frame member 60. A lock 68 secures the rod 66 relative to the frame member 60. At the top of the rod 66 is an I.V. block 70. The I.V. block 70 is shown in detail in FIGS. 3 and 4.

FIG. 3 comprises an enlarged view of the apparatus 10 taken generally from oval 3 of FIG. 2. FIG. 4 is a top view of the I.V. block 70 taken generally along line 4—4 of FIG. 3. For the following discussion of the I.V. block 70, reference will primarily be made to FIGS. 3 and 4.

The I.V. block 70 comprises a generally cylindrical element secured to the top of the rod 66. At the top of the I.V. block 70 are four arms separated by grooves. The grooves essentially comprise transverse or diametrically extending grooves, with the arms at the outer periphery of the block 70. The spaced apart arms define the groove elements between them.

There are four arms 72, 76, 80, and 84, which are generally of a triangular configuration and which are disposed at the outer periphery of the upper portion of the block 70. Between the arms 72 and 76 is a groove 74. Between the arms 76 and 80 is a groove 78. Between the arm 80 and the arm 84 is a groove 82. Between the arm 84 and the arm 72 is a groove 86. The grooves 74 and 82 are aligned with each other, and the grooves 78 and 86 are aligned with each other.

The use of the arms and grooves of the I.V. block 70 is illustrated in FIG. 3 in which two I.V. containers or bags 2 and 4 are shown secured to the block 70. The I.V. container or bag 2 is shown secured to the arm 84, and the I.V. bag or container 4 is shown secured to the arm 76.

The arms of the I.V. block 70 generally comprise hooks for supporting I.V. bags or containers. It will be noted that since the I.V. bags are located so close to the arm 66, essentially disposed adjacent thereto, there is no problem with a weight or moment arm, as is possible with many of the prior art elements discussed above in the "Background of the Invention" portion of the specification. Accordingly, the tendency or likelihood of tipping is substantially reduced with the apparatus of the present invention.

Extending between the vertical frame members 50 and 60 upwardly from the base 12 is a horizontal frame member 90. A handle assembly 130 is secured to the top of the vertical frame member 50 and to the vertical frame member 60 adjacent to the upper rod 66 and its lock 68. The horizontal frame member 90 is below the handle assembly 130.

A pair of hook or hanger elements 92 and 94 is secured to the horizontal frame member 90. Details of the hook or hanger elements 92 and 94 are shown in FIGS. 5, 6, and 7. FIG. 5 is an enlarged view in partial section taken generally from circle 5 of FIG. 2. FIG. 6 is a view of the hanger 94 and the horizontal frame member 90 taken generally along line 6—6 of FIG. 5. FIG. 7 is a front view of the apparatus 10 taken generally along line 7—7 of FIG. 2.

Extending between the horizontal frame member 90 and the front frame member 14 of the base 12 is a diagonal frame member 110.

The diagonal frame member 110 provides structural integrity and strength for the frame by transferring forces from the frame members 50 and 60 to the base 12 through the members 92 and 14. The stability of the apparatus 10 is thus enhanced by the diagonal member 110. Essentially, the load of a user of the apparatus 10 is spread by the vertical frame members 50 and 60 and the diagonal frame member 110 to the entire base 12. This, of course, helps to prevent tipping and promotes stability. The balancing of a load over or on the entire base is thus accomplished by the frame which includes vertical, horizontal, and diagonal members.

The diagonal frame member 110 also serves as a convenient location for supporting active functional elements, such as electrical elements. A power strip 112 is shown secured to the frame member 110. An electric cord 114 extends from the power strip 112 to be plugged into a receptacle on a wall, etc. In FIG. 7, two infusion pumps 6 and 8 are shown in dash/dot line schematically represented as being secured to the front of the vertical frame members 50 and 60. The pumps are also schematically illustrated in dash dot line as having their plugs connected to the power strip 112. The pump 8 is also shown in FIG. 2 in dash dot line.

In FIG. 9, which is a view in partial section taken generally along ling 9—9 of FIG. 7, the power strip 112 is shown secured to the diagonal frame member 110. The electric cord for the pump 8 is shown connected to the power strip 112.

The electrical cord for the power strip 112, when not in use may conveniently be wound about the hook elements 92 and 94 for storage purposes.

The handle assembly 130 is shown in FIGS. 1, 2, 7, and 8. For the following discussion of the handle assembly 130, reference will primarily be made to those Figures.

The handle assembly 130 includes a horizontal or transverse element 132 which is connected to the vertical frame members 50 and 60. Extending diagonally downwardly and rearwardly from the outer ends of the transverse or horizontal element 132 are two handle members 134 and 140. A pair of horizontal elements extend inwardly from the lower portions of the frame members 134 and 140. They include handle members 136 and 142, respectively. Extending diagonally upwardly, generally parallel to the members 134 and 140, are handle members 138 and 144. The handle members 138 and 144 extend upwardly and inwardly from the inner ends of the handle members 136 and 142, respectively.

The handle assembly 130 affords a plurality of appropriate gripping elements to be used by virtually any type of user of the apparatus 10. A user may grasp the horizontal or transverse handle member 132, the outer diagonal handle members 134, and 140, the bottom horizontal handle members 136 and 142, or the inner diagonal handle members 138 and 144. In the alternative, a user may grasp any combination of the handle members as convenient and as appropriate for the needs of the individual ambulatory patient who is the user of the apparatus 10.

In FIG. 7, a small infusion pump 150 is shown in dash dot line secured to the horizontal handle element 132. The elements of the handle are preferably made of the same size tubing as are the members 50 and 60. The convenience of such sizing provides versatility in securing various items to the various elements or members of the apparatus 10.

FIG. 10 is a perspective view of an I.V. hangar 160, which comprises an alternate embodiment of the I.V. block 70 for holding an I.V. bag and the like. The alternate embodiment I.V. holder 160 includes three separate holder elements. The holder apparatus 160 includes a center vertical element 162. On the bottom of the element 162 is a threaded portion 164. The threaded portion 164 may conveniently be secured to an upper rod element, such as the upper rod element 66 to which the I.V. block 70 is secured.

At the upper portion of the vertical element 162 is a crown 166. A crown 166 comprises a front crown and is generally aligned with a rear crown 174. Extending laterally outwardly and slightly downwardly from the front crown 166 is a front arm 168. At the distal end of the arm 168 is an outer hook element 170. the hook element 170 essentially comprises an inverted U element. Extending upwardly from the outer hook 170, and generally parallel to the arm 168, is a rear arm 172. The arm 172 extends upwardly from the bottom of the hook element 170 to the rear crown 174. Extending downwardly and outwardly from the rear crown 174 is a rear side arm 176. The arm 176 terminates in an outer hook element 178 remote from the crown 174.

The outer hook element 178 is also a U-configured element. Extending upwardly and inwardly from the bottom of the outer hook 178, and generally parallel to the arm 176, is a front arm 180. The front arm 180 terminates in an end 182 adjacent to the crown 166. The end 182 is spaced apart slightly from the crown 166 to allow an I.V. bag to be inserted onto the arm 180, is desired.

The hook elements 170 and 178, along with their adjacent arms 168, 172 and 176, 180, respectively, comprise essentially mirror images of each other. The arms 168 and 172 are generally parallel to each other, as are the arms 176 and 180.

I.V. bags may be conveniently disposed over the outer hook elements 170 and 178 and also over the front arm 180, as desired. The downward and outward slope of the arms 168, and 172 from the crowns 166 and 174, as well as the slope of the arms 176 and 180 serve to insure that the I.V. bags will remain securely on the holder apparatus 160, at the same time, the bags may easily be disposed on and removed from the hooks and the rear hooks 170 and 178 and the arm 180 easily and conveniently.

It will be noted that the base 12 comprises a relatively large and thus stable base for the apparatus 10. The console and walker apparatus 10 supports I.V. solution bags and the infusion pumps for them, as well as the electrical components necessary for operating the pumps. In addition, other elements, as necessary, required or desirable for an ambulatory patient, may also be carried by the apparatus as it is wheeled or moved by the ambulatory patient.

Finally, the handle assembly 130 allows an ambulatory patient to hold onto the apparatus 10 in a variety of ways, as convenient or desirable by the patient. It will be noted that the I.V. solution bags or containers may be supported conveniently in a cluster, and not spread out. In the cluster, they are convenient for the user of the apparatus and not dangling in a spaced apart orientation.

It will also be noted that the relatively large infusion pumps 6 and 8 are disposed generally over the base 12, and thus their weight does not adversely affect the stability of the apparatus 10.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, within the limits only of the true spirit and scope of the invention.

What I claim is:

1. Portable intravenous equipment console and walker apparatus comprising in combination:

base means for providing support and stability;

wheel means secured to the base means for moving the base means;

frame means secured to and extending upwardly from the base means for supporting intravenous equipment;

handle means secured to the frame means to which a user holds onto for walking including a first element extending generally horizontal, a second element extending diagonally downwardly from the first element, a third element extending inwardly from the second element remote from the first element, a fourth element extending diagonally upwardly from the third element remote from the first element, a fifth element extending downwardly from the first element generally parallel to and spaced apart from the second element, a sixth element secured to and extending inwardly form the fifth element and generally aligned with the third element, and a seventh element secured to and extending diagonally upwardly from the sixth element and generally parallel to and spaced apart from the fourth element.

2. The apparatus of claim 1 in which the frame means for supporting intravenous equipment includes an I.V. block having a plurality of arms separated by a plurality of grooves.

3. The apparatus of claim 1 in which the frame means for supporting intravenous equipment includes a first frame member secured to and extending upwardly from the base means and a second frame member secured to and extending upwardly from the base means and spaced apart from the first frame member.

4. The apparatus of claim 3 in which the handle means is secured to the first and second frame members.

5. The apparatus of claim 4 in which the first element of the handle means extends between and is secured to the first and second frame members.

6. The apparatus of claim 5 in which the frame means further includes a diagonal frame member secured to the base means and to the first and second member.

7. The apparatus of claim 6 in which the frame means further includes a third frame member secured to and extending between the first and second frame members, and the diagonal frame member is secured to the third member.

8. The apparatus of claim 3 in which the frame means further includes a fourth frame member telescopingly secured to the first frame member.

9. The apparatus of claim 8 in which the frame means further includes an I.V. block secured to the fourth frame member.

10. The apparatus of claim 9 in which the I.V. block comprises a plurality of upwardly extending fingers separated by a plurality of grooves.

11. The apparatus of claim 8 in which the frame means further includes an I.V. holder secured to the fourth frame member.

12. The apparatus of claim 1 in which the base means includes a basket.

13. The apparatus of claim 1 in which the wheel means includes a pair of primary wheels and a pair of caster wheels.

14. The apparatus of claim 1 in which the base means includes a front frame member, a rear frame member, and a pair of side frame members spaced apart from each other and secured to the front and rear frame members.

15. The apparatus of claim 14 in which the frame means includes first and second vertical frame members secured to and extending upwardly from the rear frame member of the base means.

16. The apparatus of claim 14 in which the base means further includes a basket within the front, rear, and side frame members.

17. The apparatus of claim 1 in which the frame means includes a first frame member, and the intravenous equipment includes an intravenous solution bag and an infusion pump for pumping the solution in the bag secured to the first frame member.

18. The apparatus of claim 17 in which the frame means further includes a second frame member, and a power strip is secured to the second frame member for providing electrical power for the infusion pump.

19. Handle apparatus for a wheeled walker having a frame extending upwardly from the wheels comprising in combination:

a first element extending generally horizontally from the frame;

a second element extending generally diagonally downwardly from the first element;

a third element extending generally inwardly from the second element; and a fourth element extending generally diagonally upwardly from the third element and remote from the first element.

20. The apparatus of claim 19 which further includes:

a fifth element extending generally diagonally downwardly from the first element generally parallel to and spaced apart from the second element;

a sixth element extending generally inwardly from the fifth element and generally aligned with the third element; and a seventh element extending generally diagonally upwardly from the sixth element and generally parallel to and spaced apart from the fourth element.

21. Walker apparatus comprising in combination:

base means for providing support and stability;

wheel means secured to the base means for moving the base means;

frame means secured to and extending upwardly from the base means for supporting handle means;

handle means secured to the frame means to which a user holds onto for walking including

- a first element secured to the frame means and extending generally horizontal and having first and second ends,
- a second element extending diagonally downwardly from the first element from the first end,
- a third element extending inwardly from the second element remote from the first element, and
- a fourth element extending diagonally upwardly from the third element remote from the first element.

22. The apparatus of claim 21 in which the handle means further includes

- a fifth element extending downwardly from the first element at the second end and generally parallel to and spaced apart from the second element,
- a sixth element secured to and extending inwardly from the fifth element and generally aligned with the third element, and
- a seventh element secured to and extending diagonally upwardly from the sixth element and generally parallel to and spaced apart from the fourth element.

* * * * *